US006171549B1

(12) United States Patent
Kent

(10) Patent No.: US 6,171,549 B1
(45) Date of Patent: Jan. 9, 2001

(54) METHOD FOR STERILIZING PRODUCTS

(75) Inventor: Randall S. Kent, Thousand Oaks, CA (US)

(73) Assignee: SteriSure, Inc., Los Angeles, CA (US)

( * ) Notice: Under 35 U.S.C. 154(b), the term of this patent shall be extended for 0 days.

(21) Appl. No.: 08/573,149

(22) Filed: Dec. 15, 1995

Related U.S. Application Data

(63) Continuation-in-part of application No. PCT/CA94/00401, filed on Jul. 22, 1994, which is a continuation-in-part of application No. 08/095,698, filed on Jul. 22, 1993, now Pat. No. 5,362,442.

(51) Int. Cl.$^7$ ................................. A01N 1/02; A61L 2/08
(52) U.S. Cl. ..................................... 422/22; 435/2
(58) Field of Search ............................... 422/22, 23, 41, 422/44; 435/235.1, 236, 2

(56) References Cited

U.S. PATENT DOCUMENTS

| | | |
|---|---|---|
| 2,832,689 | 2/1958 | Proctor . |
| 2,920,969 | 1/1960 | Stoddard . |
| 2,962,380 | 11/1960 | Wertheim . |
| 3,620,944 | 11/1971 | Tanito . |
| 4,620,908 | 11/1986 | Van Duzer . |
| 4,933,145 | 6/1990 | Uchida et al. . |
| 5,134,295 | 7/1992 | Wälischmiller . |
| 5,185,371 * | 2/1993 | Rubinstein ............... 422/28 |
| 5,226,065 | 7/1993 | Held et al. . |
| 5,418,130 * | 5/1995 | Platz et al. ............... 435/2 |
| 5,712,086 | 1/1998 | Horowitz et al. ............... 435/2 |

FOREIGN PATENT DOCUMENTS

| | | |
|---|---|---|
| 2056619 | 4/1991 | (CA) . |
| 334 679 A2 | 3/1989 | (EP) . |
| WO 90/00907 | 2/1990 | (WO) . |
| WO 91/16060 | 4/1991 | (WO) . |

OTHER PUBLICATIONS

Defeng, Zeng, et al. "Sterilization of silver acidum . . . by radioactive cobalt–60 gamma ray," *Radiat. Phys. Chem.*, pp. 643–646, 1995.*

"AABB FDA Liaison Meeting," *ABC Newsletter*, Dec. 12, 1997, p. 14.

Richard J. Davey, MD, "The Effect of Irradiation on Blood Components," in Michael L. Baldwin et al., eds.,, *Irradiation of Blood Components*, Bethedsa, MD: American Association of Blood Banks, 1992, pp. 51–62.

D. E. Wyatt et al., "Is There Life After Irradiation?" Part 1, *Bio. Pharm.* Jun. 1993, pp. 34–39.

D. E. Wyatt et a., "Is There Life After Irradiation?" Part 2, *Bio. Pharm.*, Jul.–Aug. 1993, pp. 46–52.

Leitman, S. F., Use of Blood Cell Irradiation in the Prevention of Post Transfusion Graft–vs–Host Disease, *Transfus. Sci.* 1989; 10:219–232.

Martindale's Extra Pharmacopoecia, Glucose p. 1265; prior art.

The Merck Index, Eleventh Edition Glucose pp. 4353–4354, prior art.

* cited by examiner

*Primary Examiner*—Elizabeth McKane
(74) *Attorney, Agent, or Firm*—Oliff & Berridge, PLC

(57) ABSTRACT

A method for sterilizing products to inactivate biological contaminants such as viruses, bacteria, yeasts, molds, mycoplasmas and parasites is disclosed. The method involves irradiating the product at a low dose rate from about 0.1 kGy/hr. to about 3.0 kGy/hr. for a period of time sufficient to sterilize the product. The method does not destroy sensitive materials such as blood and blood components. Further, the method does not require pre-treatment of the product such as freezing, filtration or the addition of chemical sensitizers.

19 Claims, No Drawings

METHOD FOR STERILIZING PRODUCTS

This application is a continuation in part of PCT/CA94/00401 filed Jul. 22, 1994 which is a continuation-in-part of U.S. Ser. No. 08/095,698 filed Jul. 22, 1993, now U.S. Pat. No. 5,362,442.

FIELD OF THE INVENTION

The present invention relates to a method for sterilizing products to inactivate biological contaminants such as viruses, bacteria, yeasts, molds, mycoplasmas and parasites.

BACKGROUND OF THE INVENTION

Several products that are prepared for human, veterinary or experimental use may contain unwanted and potentially dangerous contaminants such as viruses, bacteria, yeasts, molds, mycoplasmas and parasites. Consequently, it is of utmost importance that any biologically active contaminant in the product be inactivated before the product is used. This is especially critical when the product is to be administered directly to a patient, for example in blood transfusions, organ transplants and other forms of human therapies. This is also critical for various biotechnology products which are grown in media which contain various types of plasma and which may be subject to mycoplasma or other viral contaminants.

Previously, most procedures have involved methods that screen or test products for a particular contaminant rather than removal or inactivation of the contaminant from the product. Products that test positive for a contaminant are merely not used. Examples of screening procedures include the testing for a particular virus in human blood from blood donors. However, such procedures are not always reliable and are not able to detect the presence of viruses in very low numbers. This reduces the value or certainty of the test in view of the consequences associated with a false negative result. False negative results can be life threatening in certain cases, for example in the case of Acquired Immune Deficiency Syndrome (AIDS). Furthermore, in some instances it can take weeks, if not months, to determine whether or not the product is contaminated.

More recent efforts have focused on methods to remove or inactivate contaminants in the products. Such methods include heat treating, filtration and the addition of chemical inactivants or sensitizers to the product. Heat treatment requires that the product be heated to approximately 60° C. for about 70 hours which can be damaging to sensitive products. Heat inactivation can destroy up to 50% of the biological activity of the product. Filtration involves filtering the product in order to physically remove contaminants. Unfortunately this method may also remove products that have a high molecular weight. Further, in certain cases small viruses may not be removed by the filter because of the larger molecular structure of the product. The procedure of chemical sensitization involves the addition of noxious agents which bind to the DNA/RNA of the virus and which are activated either by UV or ionizing radiation to produce free radicals which break the chemical bonds in the backbone of the DNA/RNA of the virus or complex it in such a way that the virus can no longer replicate. This procedure requires that unbound sensitizer is washed from cellular products since the sensitizers are toxic, if not mutagenic or carcinogenic, and can not be administered to a patient.

Irradiating a product with gamma irradiation is another method of sterilizing a product. Gamma irradiation is effective in destroying viruses and bacteria when given in high total doses. (Keathly, J. D. Et al.; Is There Life after Irradiation? Part 2; BioPharm July–August, 1993, and Leitman, Susan F.; Use of Blood Cell Irradiation in the Prevention of Post Transfusion Graft-vs-Host Disease; Transfusion Science 10:219–239, 1989). However, the published literature in this area teaches that gamma irradiation can be damaging to radiation sensitive products such as blood. In particular, it has been shown that high radiation doses are injurious to red cells, platelets and granulocytes (Leitman, ibid). Van Duzer, in U.S. Pat. No. 4,620,908 discloses that the product must be frozen prior to irradiation in order to maintain the viability of a protein product. Van Duzer concludes that:

"If the gamma irradiation were applied while the protein material was at, for example, ambient temperature, the material would be also completely destroyed, that is the activity of the material would be rendered so low as to be virtually ineffective."

Unfortunately, many sensitive biologicals, such as blood, would lose viability and activity if subjected to freezing for irradiation purposes and then thawing prior to administration to a patient.

SUMMARY OF THE INVENTION

In view of the above, there is a need to provide a method of sterilizing products that is effective in removing biological contaminants while at the same time having no adverse effect on the product. The present invention has shown that if the irradiation is delivered at a low dose rate, then sterilization can be achieved without harming the product. No prior references have taught or suggested that applying gamma irradiation at a low dose rate can overcome the problems admitted in the prior references.

Accordingly, the present invention provides a method for sterilizing a product comprising irradiating the product with gamma irradiation at a rate from about 0.1 kGy/hr. to about 3.0 kGy/hr. for a period of time sufficient to sterilize the product.

The rate of irradiation can be specifically from about 0.25 kGy/hr. to about 2.0 kGy/hr., more specifically from about 0.5 kGy/hr. to about 1.5 kGy/hr. and even more specifically from about 0.5 kGy/hr. to about 1.0 kGy/hr.

The term "sterilize" as used in the present application generally means to inactivate any biological contaminant present in the product.

The length of time of irradiation or the total dose of irradiation delivered will depend on the bioburden of the product, the nature of the contaminant and the nature of the product.

Higher doses of irradiation are required to inactivate viruses as compared to bacteria. For example, using the dose rates of the present invention, one may use an irradiation time of greater than 10 hours to eliminate viral contamination in contrast to an irradiation time of only 45 minutes to remove bacterial contamination.

The process according to the present invention can be carried out at ambient temperature and does not require the heating, freezing, filtration or chemical treatment of the product before the process is carried out. This offers another significant advantage of the present process as it avoids some of the extra treatment steps of the prior art processes.

Certain products, such as blood, may be diluted prior to irradiation. Diluting the product may serve to reduce degradation of the product during irradiation. The choice of diluent depends on the nature of the product to be irradiated. For example, when irradiating blood cells one would choose a physiologically acceptable diluent such as citrate phosphate dextrose.

In cases where living cells (such as blood cells) are to be irradiated, a scavenger may be added to bind free radicals and other materials that are toxic to cells. A suitable scavenger is ethanol.

The efficacy of the method of the present invention is contrary to what others skilled in this area have observed or predicted. (U.S. Pat. No. 4,620,908 and Susan Leitman, ibid). The method provides a method of irradiating products that is not harmful to the product itself. In particular, the method of the present invention can effectively sterilize a product as fragile as blood without destroying the viability of the cells contained therein. Consequently the method of the present invention offers a significant technical and scientific advancement to the sterilization field. The method also provides an invaluable service to health care and the general public by providing a method to produce safe and sterile products for human use. This is especially critical in light of the spread of viral diseases such as AIDS and hepatitis through the transfusion of contaminated blood and blood products.

DESCRIPTION OF PREFERRED EMBODIMENTS

The following examples are provided in order to illustrate the method of the present invention and are not meant to limit the scope of the invention.

EXAMPLE 1

Sterilization of Blood

A 200 ml bag of one day old packed red blood cells was used. Ethanol was added to the cells in order to achieve a final ethanol concentration of 0.01% v/v. The red blood cells were diluted by a factor of one in ten using a modified Citrate Phosphate Dextrose (CPD) solution having a pH of about 6.4 to 6.7 and having the following composition in a total volume of 500 ml:

Citric Acid Monohydrate 0.2 g

Sodium Citrate Dihydrate 26.3 g

Sodium Monobasic Phosphate 2.2 g

Sodium Dibasic Phosphate 1.0 g

Dextrose 3.2 g

The cells were irradiated in a commercial size gamma irradiator which contained a cobalt 60 source rack. Irradiation was done off carrier in an unprotected box. The cells were irradiated for twenty four hours at a rate of approximately 1 kGy/hr. After the irradiation period the red blood cells were examined visually and were found to be viable, having a brilliant red colour. A control sample, consisting of packed red blood cells that were not diluted with the above-described CPD solution, was not viable after irradiation.

Four days after the irradiation procedure, the diluted cells were tested for levels of various blood components and the results are shown in Table 1. The control sample consisted of blood from the same bag as the test sample but it did not undergo irradiation. Table 1 illustrates that dilution and irradiation of human blood cells did not significantly alter the white blood cell count. The platelet count and hematocrit values were slightly lower than the control; however, these values are still within the range that is seen in normal adult blood. The level of hemoglobin was higher than in the control indicating that some red blood cells did lyse during the procedure. This is also evidenced by the lower red blood cell count. Nevertheless, contrary to what has been previously published, up to 25 kGy of radiation did not destroy the components of blood by the present procedure. The cells were also counted and found to be viable after 25 kGy of gamma irradiation delivered at a low dose rate of 1 kGy/hr.

TABLE 1

| Component | Irradiated Blood | Control Blood |
|---|---|---|
| White Blood Cells | 4 K/mm$^3$ | 4.8 K/mm$^3$ |
| Red Blood Cells | 3 Mi/mm$^3$ | 7.2 Mi/mm$^3$ |
| Hemoglobin | 42 g/dl | 21 g/dl |
| Hematocrit | 46% | 64% |
| Platelet | 100 k/mm$^3$ | 120 k/mm$^3$ |

EXAMPLE 2

Sterilization of Dextrose

Dextrose (or glucose) containing solutions are used in the treatment of carbohydrate and fluid depletion, in the treatment of hypoglycaemia, as a plasma expander, in renal dialysis and to counteract hepatotoxins (The Merck Index, Eleventh Edition; Merck & Co. Inc., 1989 and Martindale's Extra Pharmacopecia p. 1,265). Dextrose is also the preferred source of carbohydrate in parental nutrition regimens (The Merck Index, Eleventh Edition; Merck & Co. Inc., 1989 and Martindale's Extra Pharmacopecia p. 1,265). In all of the above applications, the dextrose must be sterilized before use. Sterilization of dextrose containing products is generally done by heat sterilization or autoclaving. Unfortunately, these methods have been reported to degrade or caramelize dextrose containing solutions resulting in a colour change in the solution (Martindale's Extra Pharmacopecia p. 1,265). Gamma irradiation of glucose has also been reported to decompose glucose containing solutions (Kawakishi et al.; Radiation-Induced Degradation of D-glucose in Anaerobic Condition. Agric.Biol.Chem. June, 1977). Therefore, there is a need for a method that can sterilize dextrose containing products that does not degrade the product itself. In view of the problems of the prior art, a dextrose solution was treated according to the method of the present invention as follows.

A 5% dextrose solution was irradiated for 24 hours, at a rate of approximately 1 kGy/hr. After irradiation the product was tested and it was found that there was no visible light spectrum change as compared to the non-irradiated control. Therefore, the present method can be useful in sterilizing products that contain dextrose.

In addition to the above experiment, fresh solutions of 5% and 50% dextrose were irradiated to 25 kGy over 36 hours at ambient temperature. The results were similar to those described above. In addition, UV/VIS scans were obtained and demonstrated a complete absence of the peak at 283.4 nm for "furfurals" as per U.S.P. In contrast, dextrose samples sterilized using an autoclave contain the 283.4 furfural peak. "Furfurals" are carcinogenic.

EXAMPLE 3

Sterilization of Human Serum Albumin

Normal Human Serum Albumin was irradiated as a 25% salt-poor solution to a total dose of 25 kGy over 36 hours using a Gammacell 220 (Co$^{60}$ is the gamma ray source in this instrument). The temperature was not controlled during the irradiation but it is estimated that the container holding the albumin solution was approximately 23° C. The results of HPLC analysis are given in Table 2.

TABLE 2

| PARAMETER | CONTROL (%) | IRRADIATED (%) |
|---|---|---|
| Polymer | 2 | 3 |
| Dimer | 7 | 8 |
| Monomer | 90 | 86 |
| Low Molecular Weight | 1 | 3 |
| pH | 7.05 | 6.97 |
| NTU (must be >20) | 11.4 | 11.4 |

As the results demonstrate, Normal Human Serum Albumin can safely be irradiated to 25 kGy (at a rate of approximately 0.7 kGy/hr.) at room temperature without adversely affecting the essential properties of the protein. This has not been demonstrated before. All other attempts at irradiating serum albumin require that it be irradiated in the frozen stage. This adds to the cost and difficulty of doing the irradiation.

EXAMPLE 4

Normal human blood from a healthy donor was taken in a heparinized tube, washed three times with standard CPD solution, then diluted 1:20 with CPD containing 0.01% v/v Ethanol. This latter solution of CPD with 0.01% v/v Ethanol is called SCPD. Two ml aliquots were then placed in 10 ml plastic test tubes and irradiated to different doses up to 26 kGy over 36 hours at room temperature. There was no haemolysis and the cells appeared intact if somewhat large and slightly irregular in shape. The results of three separate experiments are reported in Table 3.

TABLE 3

| PARAMETER | RBC[1] | HGB[2] | HCT[3] | MCV[4] | MCH[5] | MCHC[6] | RDW[7] | FLAGS |
|---|---|---|---|---|---|---|---|---|
| 1* | 1.08 | 41 | .097 | 89.5 | 38.3 | 427 | 17.7 | Nearly Normal |
| CONTROL | .99 | 33 | .089 | 90.2 | 33.0 | 366 | 15.3 | |
| 2* | | | | 95.0 | 32.3 | 339 | 12.0 | |
| 12 kGy 1 | 1.22 | 45 | .166 | 135.8 | 36.5 | 269 | 27.3 | 1 + Anisocytosis |
| | 1.38 | 45 | .199 | 144.7 | 33.0 | 228 | 24.9 | 3 + Macrocytocis |
| 1 | 1.04 | 32 | .169 | 163.0 | 31.3 | 192 | 18.8 | 1 + Anisocytosis |
| 16 kGy | 0.54 | 29 | .088 | 162.5 | 54.5 | 335 | 18.8 | 3 + Macrocytocis |
| 2 | 0.82 | 27 | .128 | 156.5 | 32.8 | 209 | 19.8 | 2 + Anisocytosis |
| | 0.81 | 26 | .124 | 152.6 | 32.4 | 212 | 20.2 | 3 + Macrocytocis |
| 1 | 0.79 | 244 | .125 | 158.4 | 30.8 | 194 | 19.4 | 1 + Anisocytosis |
| 20 kGy | 1.26 | 28 | .203 | 161.5 | 22.1 | 137 | 19.0 | 3 + Macrocytocis |
| 2 | 0.93 | 30 | .141 | 151.5 | 32.3 | 213 | 20.1 | 2 + Anisocytosis |
| | 0.92 | 30 | .143 | 155.5 | 32.1 | 207 | 20.5 | 3 + Macrocytocis |
| 26 kGy 1 | 1.15 | 34 | .180 | 155.9 | 29.4 | 189 | 19.3 | 1 + Anisocytosis |
| | 1.15 | 34 | .176 | 153.0 | 29.9 | 195 | 23.4 | 3 + Macrocytocis |

*Experiment 1 and Experiment 2
[1]Red Blood Cell Count: Cells × $10^{12}$/liter
[2]Hemoglobin: grams/liter
[3]Hematocrit
[4]Mean Corpuscular Volume: Femtoliters
[5]Mean Corpuscular Hemoglobin: picograms
[6]Mean Corpuscular Hemoglobin Concentration: grams/liter The cells were easily put into suspension and reconstituted in fresh buffer.

The following three experiments (Examples 5, 6 and 7) were conducted in order to determine the efficacy of the method when treating HIV-contaminated blood. In each Example the cells were similarly treated. In these experiments, the cells were gently agitated after 12, 16 and 24 hours of irradiation. Further, in the third experiment, (Example 7), the cells were placed in T25 flasks to provide greater surface area and reduce the concentration due to settling in the bottom of the centrifuge tubes. In each case, the cells were irradiated at a dose rate of approximately 0.7 kGy/hr.

EXAMPLE 5

Sterilization of HIV-containing Blood

The following experiment was undertaken with the following specific objectives:

1. To evaluate the toxicity of the process towards red blood cells (RBCs).
2. To evaluate the anti-retroviral activity of the process.

Procedure

Initially, 2 ml of anticoagulated blood was obtained from an HIV-seronegative donor. The blood was centrifuged, and the plasma was removed. The remaining cell pellet was resuspended in 10 ml of the CPD buffer and centrifuged. This washing process was repeated a total of three times. The final pellet was resuspended in 40 ml of the SCPD buffer, and distributed into plastic tubes in 2 ml aliquots, with 16 separate aliquots being retained for further manipulation. For 8 of these tubes, an aliquot of HTLV-IIIB was added. This is a laboratory strain of the HIV virus and 100 tissue culture infective doses (TCID) were added to each of the tubes to be infected. For the remaining 8 tubes, a "mock" infection was performed, by adding a small amount of non-infectious laboratory buffer, phosphate buffered saline (PBS). Four infected and four non-infected tubes were subjected to the process. For comparison, the remaining 8 tubes (four infected and four non-infected) were handled in an identical manner, except that they were not subjected to the process.

It should be stated that at the beginning of the study, a separate aliquot of blood was obtained from the donor. This was processed in the clinical hematology laboratory and a complete hemogram was performed. These baseline results were compared to repeat testing on the study aliquots, which included evaluation of four processed and four unprocessed samples, all of which were not infected with HIV.

An aliquot of 0.5 ml of each of the infected study samples was inoculated on mononuclear cells (MCs) which had been obtained three days earlier. These cells had been suspended in RPMI culture medium, with 10% fetal calf serum and other additives (penicillin, streptomycin, glutamine and HEPES buffer) along with 1 ug/ml PHA-P. At the same time as this inoculation, the cells were resuspended in fresh medium with rIL-2 (20 U/mi). The cultures were maintained for 7 days. Twice weekly, a portion of the culture medium was harvested for the measurement of HIV p24 antigen levels (commercial ELISA kit, Coulter Electronics, Hialeah, Fla.) for the measurement of viral growth.

A separate aliquot of the eight infected study samples was used for viral titration experiments. Briefly, serial four-fold dilutions of the virus-containing fluids (ranging from 1:16 to 1:65,536) were inoculated in triplicate in 96-well flat-bottom tissue culture plates. PHA-stimulated MCs were added to each well (4 million cells in 2 ml culture medium, with IL-2). An aliquot of the supernatant from each culture well was harvested twice weekly for the measurement of HIV p24 antigen levels. A well was scored as "positive" if the HIV p24 antigen value was >30 pg/ml.

The viral titer was calculated according to the Spearman-Karber method (see ACTG virology protocol manual) using the following equation:

$$M = xk + d[0.5 - (1/n)r]$$

M: titer (in log 4)

xk: dose of highest dilution d: space between dilutions n: number of wells per dilution r: sum of total number of wells Results Red blood cell parameters for the baseline sample as well as for the unprocessed and processed study samples are shown in Table 4.

TABLE 4

| Sample/Number | MCV | MCH | MCHC |
|---|---|---|---|
| Baseline | 94.5 | 32.0 | 339 |
| Unprocessed-1 | 91.4 | 34.4 | 376 |
| Unprocessed-2 | 90.2 | 37.9 | 420 |
| Unprocessed-3 | 92.1 | 40.0 | 433 |
| Unprocessed-4 | 91.0 | 40.2 | 442 |
| Processed-1 | 133.4 | 37.8 | 284 |
| Processed-2 | 131.5 | 45.0 | 342 |
| Processed-3 | 128.5 | 38.9 | 303 |
| Processed-4 | 131.1 | 39.4 | 301 |

The abbreviations used in Table 4 are explained under Table 3.

As described above, HIV cultures were established using 0.5 ml aliquots of unprocessed and processed study samples. P24 antigen levels (pg/ml) from the study samples on day 4 and day 7 of culture are shown in Table 5.

TABLE 5

| Sample/Number | p24-DAY 4 | p24-DAY 7 |
|---|---|---|
| Unprocessed-1 | 1360 | 464 |
| Unprocessed-2 | 1180 | 418 |
| Unprocessed-3 | 1230 | 516 |
| Unprocessed-4 | 1080 | 563 |
| Processed-1 | 579 | 241 |
| Processed-2 | 760 | 303 |
| Processed-3 | 590 | 276 |
| Processed-4 | 622 | 203 |

Finally, one unprocessed sample and one processed sample were selected for the performance of direct viral titration without culture. The results are shown in Table 6.

TABLE 6

| Sample/Number | Titer (log 10 ml) |
|---|---|
| Unprocessed-1 | 1.5 |
| Processed-1 | 0.0 |

The red blood cells were minimally affected by the process, although some reproducible macrocytosis was observed. Although on co-culturing of processed samples, there appeared to be some residual live virus, this was not confirmed by direct titration experiments.

EXAMPLE 6

The objective of this experiment was to evaluate the toxicity of the process towards red blood cells in a comprehensive manner.

Methods

For this experiment, 1 ml of anticoagulated blood was obtained from the same HIV-seronegative donor as in the first experiment. The blood was centrifuged and the plasma was removed. The remaining cell pellet was resuspended in 10 ml of the CPD buffer and centrifuged. This washing process was repeated a total of three times. The final pellet was resuspended in 20 ml of the SCPD buffer, and distributed into plastic tubes in 2 ml aliquots, with all 10 aliquots being retained for further manipulation. Eight tubes were subjected to the process, while the final two tubes were retained as control, unprocessed tubes. After the processing, all ten tubes were centrifuged, and the resulting pellet was resuspended in 100 ul buffer. A complete hemogram was performed on these reconcentrated study samples.

As in the first experiment, a separate aliquot of blood was obtained from the donor when the study sample was taken. A complete hemogram was performed on this baseline sample. As the study samples were re-concentrated to 33–50% of their original state, more direct comparisons with the baseline sample could be undertaken than were possible in our earlier experiment.

Results

Red blood cell parameters for the baseline sample as well as for the unprocessed and processed study samples are shown in Table 7. The abbreviations used in Table 7 are defined in Table 3.

TABLE 7

| Sample/Number | RBC | HGB | MCV | MCH | MCHC |
|---|---|---|---|---|---|
| Baseline | 4.76 | 152 | 94.9 | 31.9 | 336 |
| Unprocessed-1 | 0.99 | 33 | 90.2 | 33.0 | 366 |
| Unprocessed-2 | 1.08 | 41 | 89.5 | 38.3 | 427 |
| Processed-1 | 1.15 | 34 | 153.0 | 29.9 | 195 |
| Processed-2 | 1.15 | 34 | 155.9 | 29.4 | 189 |
| Processed-3 | 1.26 | 28 | 161.5 | 22.1 | 137 |
| Processed-4 | 0.79 | 24 | 158.4 | 30.8 | 194 |
| Processed-5 | 0.54 | 29 | 162.5 | 54.5 | 335 |
| Processed-6 | 1.04 | 32 | 163.0 | 31.3 | 192 |
| Processed-7 | 1.35 | 45 | 144.7 | 33.0 | 228 |
| Processed-8 | 1.22 | 45 | 135.8 | 36.5 | 269 |

There was macrocytosis of the cells which was present in all the processed samples. Comparable hemoglobin were measured in the unprocessed and processed samples. The absolute values were appropriate for the residual dilution. The red blood cells are preserved.

EXAMPLE 7

The objective of this experiment was to verify and expand upon the results obtained in Example 6.

Methods

For this experiment 5 ml of anticoagulated blood was obtained from the same HIV-seronegative donor as in the first two experiments. The blood was centrifuged, and the plasma was removed. The remaining cell pellet was resuspended in 100 ml of the CPD buffer, and centrifuged. This washing process was repeated a total of three times. The final pellet was resuspended in 100 ml of the SCPD buffer, and distributed in 25 ml aliquots, in T25 tissue culture flasks, with all four aliquots been retained for further manipulation. Two flasks were subject to the process, while the other two were retained as control, unprocessed flasks. After the processing, the contents of each of the flasks was observed and a visual determination of the cells capacity to absorb oxygen (turning a brighter red on exposure to ambient air) was made. Following this, the contents of the flasks were aspirated and centrifuged, with the residual pellet resuspended in a small volume of buffer. A complete hemogram was performed on these re-concentrated study samples.

As in Examples 5 and 6, a separate aliquot of blood was obtained from the donor when the study sample was taken. A complete hemogram was performed on this baseline sample. As the study samples were re-concentrated to 33–50% of their original state, direct caparisons of a number of specific parameters would be possible with the baseline sample.

Results

On visual inspection, there were no appreciable differences between the processed and unprocessed study samples. Specifically, there appeared to be a uniform distribution of well suspended cells. On exposure to ambient air, the contents of all flasks became somewhat brighter red. No specific quantitative measurements of oxygenation were made.

Red blood cell parameters for the baseline sample as well as for the unprocessed and processed study samples are shown in Table 8. The abbreviations used in Table 8 are defined under Table 3.

TABLE 8

| Sample/Number | RBC | HGB | MCV | MCH | MCHC |
|---|---|---|---|---|---|
| Baseline | 4.75 | 153 | 95.0 | 32.3 | 339 |
| Unprocessed-1 | 0.93 | 30 | 151.5 | 32.3 | 213 |
| Unprocessed-2 | 0.92 | 30 | 155.5 | 32.1 | 207 |
| Processed-1 | 0.82 | 27 | 156.5 | 32.8 | 209 |
| Processed-2 | 0.81 | 26 | 152.6 | 32.4 | 212 |

This experiment was designed to more closely approximate conditions of red blood cells to be transfused into a patient, and was consequently conducted at higher volumes. On a preliminary basis, it does not appear that the process impairs the red blood cells' ability to carry oxygen, although this should be measured more formally. Interestingly, in this experiment, there was no difference in cell size between the processed and unprocessed samples, both being large compared to baseline. Comparable haemoglobin levels were measured in all the study samples.

EXAMPLE 8

In this experiment, Immunoglobulin G (IgG) was irradiated in lyophilized form.

Method

The IgG was irradiated as a powder to a total dose of 25 kGy using a Gammacell 220. The temperature of the container holding the material was approximately 23° C. The dose rate was 0.72 kGy/hr.

Results

The results of HPLC analysis of IgG are given in Table 9. As the results demonstrate, the product appears to be unaffected after being irradiated to a dose of 25 kGy at room temperature when the irradiation is delivered at a rate of approximately 0.7 kGy/hr. This has not been previously demonstrated.

TABLE 9

| PARAMETER | CONTROL (%) | IRRADIATED (%) |
|---|---|---|
| Polymer (must be >2%) | 1 | 1 |
| Dimer | 10 | 13 |
| Monomer | 88 | 84 |
| Low Molecular Weight | 1 | 2 |

The results presented by Gergely, et al. using freeze dried IgG showed that a portion of the protein was insoluble after an irradiation dose of 12 kGy to 25 kGy at standard irradiation dose rates. (Gergely, J., Medgyesi, G. A., Igali, A. Studies of Gamma-Ray-Irradiated Human Immunoglobulin G. SM-92/12 I.A.E.A.). These results would indicate a change/degradation of the protein. In contrast, using the present method at a dose rate of approximately 0.7 kGy/hr., none of the protein was insoluble. This would indicate that little or no change or degradation of the protein occurred. Further, Gergely et al. found that a liquid formulation of human IgG lost all of its activity after irradiation. In studies using the present method on intravenous immunoglobulin (IVIG) in liquid form, it was shown that greater than 70% of a specific antibody in hyperimmune IVIG was retained.

EXAMPLE 9

In this experiment, alpha 1 proteinase inhibitor and fibrinogen were irradiated in lyophilized form.

Method

The samples were placed in a Gammacell 220 and irradiated according to the present process to a total dose of 25 kGy. Samples were then returned to the laboratory for analysis. The dose rate was 0.72 kGy/hr.

Results

The alpha 1 proteinase inhibitor, both treated and control, were 40% of a standard normal pooled plasma sample. The Mancini radial immunodiffusion technique was used as the assay.

The topical fibrinogen complex vials were reconstituted in 10 ml of water. Protamine sulphate at a concentration 10 mg/ml was added to the samples. There was instant formation of monomer in all three preparations.

EXAMPLE 10

In this experiment, Factors VII, VIII and IX were irradiated in lyophilized form.

Method

The samples were placed in a Gammacell 220 and irradiated to various total doses at a dose rate of approximately 1 kGy/hr.

Results

Factor VII retained 67% activity at 20 kGy and 75% at 10 kGy. Factor VIII retained 77% activity at 20 kGy and 88% at 10 kGy. Similarly Factor IX showed an activity level of 70% at 20 kGy and 80% at 10 kGy.

Analysis

Excellent results were found for the three Factors. To our knowledge, no one has been able to achieve these results by irradiating the Factors at ambient temperature to such a high dose of radiation with such little loss of activity. This is in direct contrast with the results of Kitchen et. al. (Kitchen, A. D. Mann, G. F., Harrison, J. F., Zuckerman, A. J. Effect of Gamma Irradiation on the Human Immunodeficiency Virus and Human Coagulation Proteins. Vox Sang 1989, 56:223–229) who found that "the irradiation of lyophilized concentrates is not a viable procedure". Similarly, Hiemstra et. al., (Hiemstra, H., Tersmette, M., Vos., A. H. V., Over, J., van Berkel, M. P. and de Bree, H. Inactivation of human immuondeficiency virus by gamma radiation and its effect on plasma and coagulation factors. Transfusion, 1991, 31:32–39) also concluded that "Gamma radiation must be disregarded as a method for the sterilization of plasma and plasma-derived products, because of the low reduction of virus infectivity at radiation doses that still give acceptable recovery of biologic activity of plasma components."

EXAMPLE 11

In this experiment, red blood cells were irradiated at a dose rate of 0.5 kGy/hr. for periods of time ranging from 7½ to 90 minutes in order to remove bacterial contaminants.

Method

Red blood cells were collected from a healthy donor in EDTA, washed 3 times with CPD solution and resuspended in CPD to provide a 1:20 dilution based on the original blood volume. The cell suspension was then subdivided into 14 tubes. To seven of the tubes approximately $1.0 \times 10^4$ Staphylococcus epidermidis were added. The cells were placed on ice for transport to the irradiation facility. All of the samples were placed in the chamber at ambient temperature and irradiated at 0.5 kGy/hr. for periods of time to give total doses of 0.0625, 0.125, 0.250, 0.375, 0.500 and 0.750 kGy respectively. The samples were removed and agitated at each time point and placed on ice for transport either to the microbiology lab or to the hematology lab for analysis.

Results

The results of the microbiology assays are given in Table 10.

TABLE 10

| RADIATION DOSE (kGy) | TIME (MIN) | NUMBER SURVIVING |
|---|---|---|
| 0 | | 92200 |
| 0.0625 | 7.5 | 84500 |
| 0.125 | 15 | 35000 |
| 0.250 | 30 | 10067 |
| 0.375 | 45 | 1800 |
| 0.500 | 60 | 250 |
| 0.750 | 90 | 0 |

Thus a dose of 0.75 kGy provides a 4.5 $\log_{10}$ reduction in bacterial survivors. This represents a significant safety factor for blood. Further, the $D_{10}$ value is approximately 0.125 kGy which corresponds well with the values reported in the literature for similar species of staphylococcus (B. A. Bridges, The effect of N-Ethylmaleimide on the radiation sensitivity of bacteria. J.Gen.Microbiol.1961, (26) 467–472 and G. P. Jacobs and N. Sadeh, Radiosensitization of Staphylococcus aureus by p-hydroxybenzoic acid.Int.J.Radiat-.Biol;. 1982, 41, 351–356).

In order to demonstrate that the red blood cells remained viable after the irradiation process, the following parameters were determined for the cells; WBC, Neutrophils, Lymphocytes, Monocytes, Eosinophils and Basophils. These determinations merely enumerated the number of cells present. All nucleated cells would, of course, be inactivated by the radiation dose delivered. The other red blood cell parameters monitored are listed in Table 11. The Methaemoglobin value was unchanged from that of the controls even after a radiation dose of 0.75 kGy. This experiment demonstrates that red blood cells can be safely irradiated by the present method to a dose of 0.75 kGy at room temperature with no loss of cell function.

Red Blood Cell Values as a Function of Radiation Dose Received

TABLE 11

| Parameter | Whole Blood | Total Dose (In kGy) | | | | |
|---|---|---|---|---|---|---|
| | | 0 | 0.0625 | 0.125 | 0.250 | 0.500 |
| RBC | 5.06 | 1.49 | 1.27 | 1.77 | 1.73 | 1.43 |
| HGB | 153 | 43 | 41 | 56 | 56 | 46 |
| HCT | .483 | .142 | .120 | .167 | .163 | .131 |
| MCV | 95.5 | 95.6 | 94.3 | 94.2 | 93.7 | 92.1 |
| MCH | 31.2 | 31.1 | 32.2 | 31.7 | 32.2 | 32.5 |
| MCHC | 327 | 325 | 341 | 336 | 344 | 353 |
| RDW | 13.3 | 12.1 | 12.7 | 12.9 | 12.9 | 13.2 |
| METHgB | 0.9 | 0.3 | 0.3 | 0.3 | 0.0 | 0.9 |

EXAMPLE 12

This experiment was conducted using the method in Example 11 to confirm the findings of Example 11 and to expand upon some of the parameters measured. The results of this experiment are given in Table 12.

Results

Red Blood Cell Values as a Function of Radiation Dose Received

TABLE 12

| PARAMETER | Total Dose (In kGy) | | | | | | |
|---|---|---|---|---|---|---|---|
| | 0 | 0.0625 | 0.125 | 0.250 | 0.375 | 0.555 | 0.750 |
| HGB | 1.8 | 1.7 | 1.8 | 1.7 | 2.0 | 2.0 | 2.0 |
| % O | 96.6 | 96.5 | 96.2 | 96.3 | 96.4 | 96.5 | 96.0 |
| % CO | 1.0 | 1.2 | 1.6 | 1.3 | 1.7 | 1.5 | 1.5 |
| % MET | 0.5 | 0.5 | −0.5 | 0.4 | −0.2 | 0.4 | 0.8 |
| % REDUCED | 1.9 | 1.9 | 2.7 | 2.2 | 2.2 | 1.7 | 1.7 |
| p60 (mm Hg) | 34 | nd | nd | nd | nd | nd | 24 |
| Hill Coefficient | 2.1 | nd | nd | nd | nd | nd | 1.8 | nd = not done
The uncertainty with the methaemoglobin levels is ± 2%; with p50 it is ± 4% (95% confidence).

These results confirm the previous results and indicate that indeed, red blood cells can be irradiated to a dose sufficient to provide 4.5 $\log_{10}$ reduction in bacteria count.

It is contemplated that future experiments will provide similar results for platelets. Thus with little or no additional manipulation, and without the addition of extraneous materials, red blood cells can be treated by the present process to provide a bacteriologically safe product, thus further reducing the risk of untoward reactions in recipients.

As evidenced by all of the above experiments, the present invention demonstrates that irradiating a product at a low dose rate from about 0.1 kGy/hr. to about 3.0 kGy/hr. is effective in sterilizing the product without adversely affecting the product itself.

While the Examples relate to specific embodiments of the method of the present invention, one skilled in the art will realize that the total time of irradiation will depend on the type of contaminant, the bioburden of the product and the nature of the product. For example, bacterial contaminants can be eliminated with very little irradiation time while viral inactivation requires a longer irradiation time. Further, extremely sensitive products, such as blood, are is preferably diluted in a physiologically acceptable diluent prior to irradiation.

It is to be appreciated that the method of the present invention can be used to treat an extremely wide variety of products that require sterilization. The fact that the present method has proven effective in blood which is a fragile biological material makes it reasonable to predict that the method can be used on many similarly sensitive products. Examples of other products that may be treated include pharmaceuticals, proteins, nucleic acids, blood components, body fluids (such as cerebral spinal fluid, saliva), liposomes, glucose containing products, cell culture media, fetal bovine serum, bone marrow, organs, foods and cosmetics such as shampoos, lotions and creams. The products may be irradiated in various forms, including, solid, liquid and lyophilized forms.

What I claim as my invention is:

1. A method for sterilizing a blood product comprising irradiating the blood product at ambient temperature and in the absence of a scavenger with gamma irradiation at a rate from about 0.1 kGy/hr. to about 3.0 kGy/hr. for a period of time sufficient to sterilize the product.

2. A method according to claim 1, wherein said irradiation is provided at a rate of from about 0.25 kGy/hr. to about 2.0 kGy/hr.

3. A method according to claim 1, wherein said irradiation is provided at a rate of from about 0.5 kGy/hr. to about 1.5 kGy/hr.

4. A method according to claim 1, wherein said irradiation is provided at a rate of from about 0.5 kGy/hr. to about 1.0 kGy/hr.

5. A method according to claim 1, wherein said product is diluted with a citrate phosphate dextrose solution.

6. A method according to claim 1, wherein said product is diluted before irradiation in a physiologically acceptable diluent to achieve a final dilution of at least 1:10.

7. A method according to claim 1, wherein said product is blood or a component thereof.

8. A method according to claim 7, wherein said product is diluted with a citrate phosphate dextrose solution.

9. A method according to claim 1, wherein said blood or blood component is diluted before irradiation in a physiologically acceptable diluent to achieve a final dilution of at least 1:10.

10. A method according to claim 9, wherein said physiologically acceptable diluent is a modified citrate phosphate dextrose solution having a pH in the range of about 6.4 to about 6.7.

11. A method according to claim 1, wherein said product contains dextrose.

12. A method according to claim 1, wherein said product is a protein.

13. A method according to claim 1, wherein said product is an antibody.

14. A method according to claim 1, wherein said product is in lyophilized form.

15. A method according to claim 14, wherein said product is selected from the group consisting of IgG, albumin, alpha 1 proteinase inhibitor, fibrinogen, Factor VII, Factor VIII and Factor IX.

16. A method according to claim 1, wherein said product is selected from the group consisting of IgG, albumin, alpha 1 proteinase inhibitor, fibrinogen, Factor VII, Factor VIII and Factor IX.

17. The method according to claim 1, wherein said product is irradiated at an ambient temperature.

18. The method according to claim 1, wherein the period of time is not less than forty-five minutes.

19. The method according to claim 1, wherein the period of time is not less than 30 minutes.

* * * * *

UNITED STATES PATENT AND TRADEMARK OFFICE
CERTIFICATE OF CORRECTION

PATENT NO. : 6,171,549 B1
DATED : January 9, 2001
INVENTOR(S) : Randall S. Kent

It is certified that error appears in the above-identified patent and that said Letters Patent is hereby corrected as shown below:

<u>Claims,</u>
1. A method for sterlizing a blood product comprising irradiating the blood product at ambient temperature and in the absence of a scavenger with gamma irradiation at a rate from about 0.1 kGy/hr. to about 3.0 kGy/hr. for a period of time sufficient to sterilize the product.

2. A method according to claim 1, wherein said irradiation is provided at a rate of from about 0.25 kGy/hr. to about 2.0 kGy/hr.

3. A method according to claim 1, wherein said irradiation is provided at a rate of from about 0.5 kGy/hr. to about 1.5 kGy/hr.

4. A method according to claim 1, wherein said irradiation is provided at a rate of from about 0.5 kGy/hr. to about 1.0 kGy/hr.

5. A method according to claim 1, wherein said product is diluted before irradiation in a physiologically acceptable diluent to achieve a final dilution of at least 1:10.

6. A method according to claim 5, wherein said physiologically acceptable diluent is a modified citrate phosphate dextrose solution having a pH in the range of about 6.4 to about 6.7.

7. A method according to claim 1, wherein said product is diluted with a citrate phosphate dextrose solution.

8. A method according to claim 1, wherein said product contains dextrose.

9. A method according to claim 1, wherein said product is a protein.

10. A method according to claim 9, wherein said product is an antibody.

11. A method according to claim 1, where said product is in lyophilized form.

UNITED STATES PATENT AND TRADEMARK OFFICE
CERTIFICATE OF CORRECTION

PATENT NO. : 6,171,549 B1
DATED : January 9, 2001
INVENTOR(S) : Randall S. Kent

It is certified that error appears in the above-identified patent and that said Letters Patent is hereby corrected as shown below:

12. A method according to claim 1, wherein said product is selected from the group consisting of IgG, albumin, alpha 1 proteinase inhibitor, fibrinogen, Factor VII, Factor VIII and Factor IX.

13. A method according to claim 11, wherein said product is selected from the group consisting of IgG, albumin, alpha 1 proteins inhibitor, fibrinogen, Factor VII, Factor VIII, and Factor IX.

14. The method according to claim 1, wherein the period of time is not less than forty-five minutes.

15. The method according to claim 1, wherein the period of time is not less than 30 minutes.

Signed and Sealed this

Twenty-ninth Day of January, 2002

*Attest:*

JAMES E. ROGAN
*Attesting Officer*  *Director of the United States Patent and Trademark Office*

UNITED STATES PATENT AND TRADEMARK OFFICE
CERTIFICATE OF CORRECTION

PATENT NO.    : 6,171,549 B1
DATED         : January 9, 2001
INVENTOR(S)   : Randall S. Kent It is certified that error appears in the above-identified patent and that said Letters Patent is hereby corrected as shown below:

<u>Column 2,</u>
Lines 62 and 63, insert the following new paragraph:
-- Ambient temperature is commonly understood as meaning the temperature of the environment in which an experiment is conducted or in which any physical or chemical event occurs. (See e.g., Hawley's Condensed Chemical Dictionary (Van Nostrand Reinhold)). --

Signed and Sealed this

Twelfth Day of November, 2002

*Attest:*

JAMES E. ROGAN
*Attesting Officer*    *Director of the United States Patent and Trademark Office*

UNITED STATES PATENT AND TRADEMARK OFFICE
CERTIFICATE OF CORRECTION

PATENT NO.    : 6,171,549 B1
DATED         : January 9, 2001
INVENTOR(S)   : Randall S. Kent It is certified that error appears in the above-identified patent and that said Letters Patent is hereby corrected as shown below:

<u>Column 2,</u>
Between lines 62 and 63, insert the following new paragraph:
-- Ambient temperature is commonly understood as meaning the temperature of the environment in which an experiment is conducted or in which any physical or chemical event occurs. (See e.g., Hawley's Condensed Chemical Dictionary (Van Nostrand Reinhold)). --

Signed and Sealed this

Fourth Day of February, 2002

JAMES E. ROGAN
*Director of the United States Patent and Trademark Office*